United States Patent [19]

Niedballa et al.

[11] Patent Number: 4,528,298

[45] Date of Patent: Jul. 9, 1985

[54] ANTIINFLAMMATORY IMIDAZOLE DERIVATIVES

[75] Inventors: Ulrich Niedballa; Irmgard Böttcher, both of Berlin, Fed. Rep. of Germany

[73] Assignee: Schering Aktiengesellschaft, Berlin and Bergkamen, Fed. Rep. of Germany

[21] Appl. No.: 516,395

[22] Filed: Jul. 22, 1983

Related U.S. Application Data

[62] Division of Ser. No. 280,163, Jul. 2, 1981, Pat. No. 4,402,960.

[30] Foreign Application Priority Data

Jul. 3, 1980 [DE] Fed. Rep. of Germany ....... 3025484

[51] Int. Cl.³ .......................................... A61K 31/415
[52] U.S. Cl. .................................................... 514/398
[58] Field of Search .............................. 548/337, 336; 424/273 R

[56] References Cited

U.S. PATENT DOCUMENTS

| | | | |
|---|---|---|---|
| 3,505,350 | 4/1970 | Doebel et al. | 426/263 X |
| 3,651,080 | 3/1972 | Doebel et al. | 424/273 R X |
| 4,182,769 | 1/1980 | Cherkofsky et al. | 424/273 R |
| 4,190,666 | 2/1980 | Cherkofsky et al. | 424/274 |
| 4,215,217 | 7/1980 | Lewis et al. | 544/139 |
| 4,330,552 | 5/1982 | Cherkofsky | 424/273 R |
| 4,402,960 | 9/1983 | Niedballa et al. | 548/337 X |

OTHER PUBLICATIONS

Bhatt, M., et al., *Current Science*, 17, 184-185 (1948).

*Primary Examiner*—Richard A. Schwartz
*Attorney, Agent, or Firm*—Millen & White

[57] ABSTRACT

Imidazole derivatives of the formula

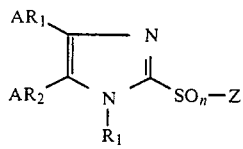

wherein $AR_1$ and $AR_2$ each independently is phenyl, optionally substituted by halogen atoms, alkyl residues, alkoxy residues; or dialkylamino residues; pyridyl, furyl; or thienyl;

$R_1$ is hydrogen; alkyl of 1-6 carbon atoms optionally; substituted by hydroxy groups, alkoxy groups, or acyloxy groups; benzyl; tetrahydropyran-2-yl; or tetrahydrofuran-2-yl n is 0, 1 or 2; and Z is phenyl optionally substituted by halogen atoms, alkyl groups, alkoxy groups, nitro groups, amino, acylamino groups or trifluoromethyl groups; pyridyl; N-oxypyridyl; pyrimidinyl; thiazolyl; or thienyl, and the physiologically acceptable salts thereof with acids, have valuable pharmacological activity, e.g., antiinflammatory activity.

3 Claims, No Drawings

ANTIINFLAMMATORY IMIDAZOLE DERIVATIVES

This is a division, of application Ser. No. 280,163, filed July 2, 1981, now U.S. Pat. No. 4,402,960.

BACKGROUND OF THE INVENTION

The present invention relates to a novel imidazole derivatives, a process for their production and pharmaceutical preparations containing them as active ingredients.

SUMMARY OF THE INVENTION

It is an object of this invention to provide new imidazole derivatives having valuable pharmacological activity.

Upon further study of the specification and appended claims, further objects and advantages of this invention will become apparent to those skilled in the These objects have been attained by providing novel imidazole derivatives of formula I

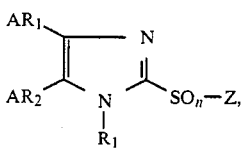

wherein
$AR_1$ and $AR_2$ each independently is phenyl, optionally substituted by halogen atoms, alkyl residues, alkoxy residues, or dialkylamino residues; pyridyl; furyl; or thienyl;

$R_1$ is hydrogen; alkyl of 1-6 carbon atoms optionally substituted by hydroxy groups, alkoxy groups, or acyloxy groups; benzyl; tetrahydropyran-2-yl; or tetrahydrofuran-2-yl;

n is 0, 1 or 2; and

Z is phenyl optionally substituted by halogen atoms, alkyl groups, alkoxy groups, nitro groups, amino, acylamino groups or trifluoromethyl groups; pyridyl; N-oxypyridyl; pyrimidinyl; thiazolyl; or thienyl, and the physiologically acceptable salts thereof with acids.

DETAILED DISCUSSION

According to this invention, the substituents $AR_1$ and $AR_2$ of the imidazoles, in each case, independently, can be phenyl, optionally substituted by halogen (F, Cl, Br, I) $C_{1-4}$-alkyl, $C_{1-4}$-alkoxy, or di-$C_{1-4}$-alkylamino; 2-, 3-, or 4-pyridyl; 2-, or 3-furyl; or 2- or 3-thienyl. Phenyl residues $AR_1$ and $AR_2$ substituted by halogen atoms include, for example, mono- or difluorophenyl or mono- or dichlorophenyl and especially p-fluorophenyl or p-chlorophenyl. Alkyl-substituted phenyl resdiues include preferably those having alkyl groups of 1-4 carbon atoms (e.g., methyl, ethyl, propyl, or isopropyl groups). Phenyl residues substituted by alkoxy groups include preferably those having alkoxy groups of 1-4 carbon atoms (e.g., methoxy, ethoxy, propoxy, or isopropoxy groups). Phenyl groups substituted by dialkylamino groups include preferably those wherein the dialkylamino residue contains 2-6 carbon atoms in total, for example, dimethylamino, methylethylamino, or diethylamino.

The heterocyclic substituents $AR_1$ and $AR_2$ include in particular, 2-pyridyl, 4-pyridyl, 2-furyl and 2-thienyl.

The phenyl residues $AR_1$ and $AR_2$ can be mono- or polysubstituted with the same or different substituents. Preferably they are monosubstituted. Preferred are phenyl residues optionally substituted in the para- position by F, Cl, $C_{1-4}$-alkyl or $C_{1-4}$ alkoxy. More preferred are phenyl, 4-fluorophenyl, 4-chlorophenyl, 4-methylphenyl or 4-methoxyphenyl. Particularly preferred is p-methoxyphenyl. It is preferred that $AR_1$ be the same as $AR_2$.

$R_1$ of the imidazole derivatives of this invention can be hydrogen; alkyl of 1-6 carbon atoms, optionally substituted by hydroxy, $C_{1-6}$ alkoxy, or $C_{1-6}$-acyloxy, such as $C_{1-6}$-alkanoyloxy; benzyl; tetrahydropyran-2-yl; or tetrahydrofuran-2-yl; preferably, $R_1$ is hydrogen, alkyl of 1-4 carbon atoms, 2-alkoxymethyl of 1-6 carbon atoms in the alkoxy group, tetrahydropyran-2-yl, or tetrahydrofuran2-yl; in particular, $R_1$ is hydrogen.

According to this invention, the substituent Z can be phenyl, optionally substituted by halogen (F, Cl, Br, I), $C_{1-4}$-alkyl, $C_{1-4}$-alkoxy, nitro, $C_{1-4}$-acylamino, such as $C_{1-6}$-alkanoylamino, or trifluoromethyl; 2-,3-, or 4-pyridyl; 2-,3- or 4-N-oxypyridyl; 2-, 3- or 4-pyrimidinyl; 2-, or 3-thiazolyl; or 2- or 3-thienyl. Preferred substituents Z are those which are also listed for $AR_1$ and $AR_2$, especially those preferred for $AR_1$ and $AR_2$.

Preferred Z are phenyl; phenyl substituted by fluorine, chlorine, bromine, alkyl of 1-4 carbon atoms, alkoxy of 1-4 carbon atoms, nitro, amino, acylamino of 1-6 carbon atoms, or trifluoromethyl; 2-pyridyl; 4-pyridyl; N-oxypyridyl; 2-pyrimidinyl; thienyl; or thiazolyl. In particular, Z is 2-thienyl, 4-fluorophenyl, 2-fluorophenyl, and 4-pyridyl.

Preferably, n is 1 or 2. Physiologically acceptable salts of the imidazole derivatives of Formula I include, for example, salts of hydrogen chloride, hydrogen bromide, hydrogen iodide, sulfuric acid, phosphoric acid, etc., or salts of organic acids, such as formic acid, acetic acid, succinic acid, maleic acid, tartaric acid or citric acid.

The novel imidazole derivatives of this invention can be prepared by following methods known per se. Suitable preparative methods including for example, a process for preparing imidazole derivatives of Formula I

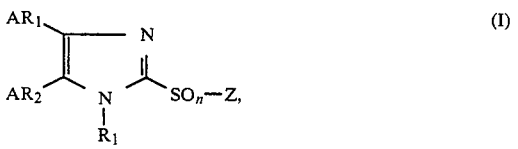

as defined above and the salts thereof with physiologically acceptable acids,
comprising conventionally
(a) condensing a compound of formula II

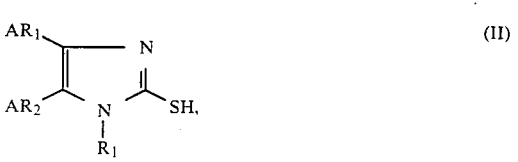

wherein $AR_1$, $AR_2$, and $R_1$ are as defined above, in the presence of a base,
with a compound of formula III

XZ (III), wherein

Z is as defined above and

X is halogen, alkylsulfonyl, arylsulfonyl, diazo, or ZI± wherein Z is as defined above; or (b) condensing a compound of formula IV

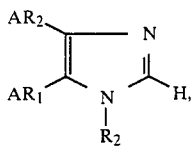

wherein

AR$_1$ and AR$_2$ are as defined above and

R$_2$ is the same as R$_1$, but is not hydrogen, in the presence of a base, with a compound of Formula V, VI, VII, VIII, or IX:

Cl—S—Z (V),

Z—S—S—Z (VI),

R$_3$—O—SO—Z (VII),

Z—S—S—Z (VIII),

Z—SO$_2$—O—SO$_2$—Z (IX), wherein

Z is as defined above and

R$_3$ is alkyl of 1-4 carbon atoms; and, optionally, subjecting the compound so produced by process (a) or (b) to oxidation, reduction, hydrolysis, alkylation and/or esterification, and/or converting these compounds into the salts thereof with physiologically acceptable acids.

The mentioned optional measures include, preferably, the oxidation of thio compounds of Formula I to the corresponding sulfinyl compounds or sulfonyl compounds; and/or the oxidation of imidazole derivatives of Formula I wherein Z is pyridyl to those wherein Z is an N-oxypyridyl residue; and/or the reduction of nitro compounds of Formula I; and/or the hydrolysis of compounds of Formula I which contain acyloxy groups, or of those imidazole derivatives wherein R$_1$ is a substituent different from hydrogen; and/or the alkylation or esterification of compounds of Formula I which contain hydroxy groups and/or amino groups and/or of those imidazole derivatives wherein R$_1$ is hydrogen.

These syntheses can be conducted under conventional conditions (Houben-Weyl, "Methoden der Org. Chemie" [Methods of Organic Chemistry] IX, Georg Thieme Publishers, Stuttgart [1955]: 116 et seq. and 229 et seq.; Chemistry Letters 1979: 939; Arch. Chim. Acad. Sci. Hung. 98: 479 [1978]; Org. Synth. 51: 128 [1971]; J. Amer. Chem. Soc. 100: 2510 and 3918 [1978]; Chem. Rev. 4: 364 [1978]; J. Org. Chem. 43: 1379 [1979]; Tetrahedron Letters 1975: 291; DOS No. 2,635,876; Rec. Trav. Chim. Pays-Bas 98: 371 [1979]; J. Med. Chem. 16: 1161 [1973]; and Bull. Soc. Chim. France 1977: 271; Dokl. Acad. Nauc. SSSR Ser. Khim. 249: 867 [1979]; all of whose disclosures are incorporated by reference herein).

After synthesis has been accomplished, the racemic imidazole derivatives of Formula I can be split conventionally into their optical antipodes, for example by chromatographing the compounds, using a column, on optically active carriers (e.g., "Sephadex"). If the synthesis is carried out according to process version (b) and optically active compounds of Formula VII or VIII are used as the starting materials, then the corresponding, optically active imidazole derivatives of Formula I are obtained directly.

The starting compounds for the processes of this invention are known or can be prepared in fully conventional manner (Zhur, Obschei Khim 31: 1093 [1961]; Synthesis 1976: 733; South African Patent No. 64/1808; J. Chem. Soc. 1963: 2135; Rec. Trav. Chim. Pays-Bas 98: 371 [1979]; DOS No. 2,635,876; Chem. Pharm. Bull. 27: 899 [1979], Houben-Weyl "Methoden der Org. Chemie" IX, Georg Thieme Publishers Stuttgart, pp. 117 et seq. and pp. 552 et seq. [1955]; Org. Synth. 51: 128 [1971]; Bull. Chem. Soc. Japan 52: 2635 [1979]; J. Med. Chem. 22: 1483 [1979]; Synthesis 1980: 32; Synthesis 1979: 181; J. prakt. Chem. 321: 495 [1979]; J. Org. Chem. 30: 633 [1965]; Rec. Trav. Chim. Pays-Bas 73: 129 [1954]; and J. Amer. Chem. Soc. 100: 2510 [1978], all of whose disclosures are incorporated by reference herein).

The imidazole derivatives of this invention are distinguished by a pronounced antiinflammatory and antiallergic activity.

Moreover, the imidazole derivatives of this inention are distinguished by a very favorable dissociation between desirable pharmacological efficacy and undesirable, especially ulcerogenic, side effects.

The antiinflammatory activity of the compounds of this invention can be determined using the conventional adjuvant arthritis test which is conducted as follows:

Female and male rats of the Lewis strain [LEW] are used in a weight range between 110 and 190 g. The animals receive drinking water and pressed feed "Altromin" ad libitum.

Ten rats are used for each dosage group.

*Mycobacterium butyricum* by Difko, Detroit, is used as the irritant. A suspension of 0.5 mg of *Mycobacterium butyricum* in 0.1 ml of thinly fluid paraffin (DAB [German Pharmacopoeia] 7) is injected at the subplantar location into the right hind paw.

The test compounds are given orally, daily, starting with the 11th day of the trial, over a period of 4 days. The compounds are administered as a clear aqueous solution or as a crystalline suspension with the addition of Myrj 53 (85 mg %) in an isotonic sodium chloride solution.

Test Setup:

The rats are divided as uniformly as possible into various groups with respect to body weight. After measuring the volume of the right hind paw by plethysmography, 0.1 ml of adjuvant is injected into the paw in the subplantar region. The right hind paws are measured from the 14th day of the experiment until the end of the test. The duration of the trial is 3 weeks.

The dose is determined at which a 40% reduction in paw volume is obtained as compared with the untreated animal (ED$_{40}$ in mg/kg body weight).

A frequent complication in therapy with nonsteroidal antiinflammatory agents is the occurrence of stomach ulcerations. This side effect can be proven by animal experiment, wherein, with a predetermined dose, the number of observed lesions and the total area thereof are measured. The ulcer test is conducted as follows.

Male Wistar rats (SPF) are utilized with a weight span of 130±10 g. The animals are put on a fast 16 hours before commencing the trial; they receive water and libitum.

Five animals are employed per dosage. The compounds are applied once orally, dissolved in sodium chloride or in the form of a crystalline suspension with the addition of 85 mg % Myrj 53.

Three hours after administering the compound, 1 ml of a 3% solution of pure diphenyl blue dye is injected intravenously, and the animal is sacrificed. The stomach is resected and examined microscopically for number of ulcers, which stand out by dye enrichment.

The dose is determined at which more than three ulcers were found per animal (="ulcerogenic dose" in mg/kg body weight).

The following table shows the results obtained in these trials with the compounds of this invention as compared with the previously known compound indomethacin (compound I) and with the structurally analogous compound III

TABLE

| No. | Compound | Adjuvant Arthritis Test $ED_{40}$ mg/kg | "Ulcerogenic Dose" in mg/kg |
|---|---|---|---|
| I | Indomethacin Prior Art | 8 | 3 |
| II | Phenylbutazone Prior Art | 50 | 80 |
| III | 4,5-Bis(4-methoxyphenyl)-2-(2-hydroxyethylsulfinyl)imidazole (DOS 2,823,197) Prior Art | 75 | larger than 400 |
| IV | 4,5-Bis(4-methoxyphenyl)-2-(4-trifluoromethylphenyl-thio)imidazole | 30 | larger than 400 |
| V | 4,5-Bis(4-methoxyphenyl)-2-phenylthioimidazole | 28 | larger than 400 |
| VI | 4,5-Bis(4-methoxyphenyl)-2-phenylsulfonylimidazole | 25 | larger than 400 |
| VII | 4,5-Bis(4-methoxyphenyl)-2-(2-thienylthio)imidazole | 20 | larger than 400 |

Surprisingly, among the compounds of this invention there are also those possessing, in addition to the antiinflammatory efficacy, likewise a pronounced antiulcerogenic and tumor-inhibiting effectiveness.

Consequently, the novel compounds, in combination with the vehicles customary in galenic pharmacy, are suitable for the treatment of, for example, acute and chronic polyarthritis, neurodermitis, bronchial asthma, hay fever, etc. It is further remarkable that the imidazole derivatives of this invention are moreover likewise suitable for the treatment of migraine and dysmenorrhea.

The specialty drug preparations are produced in the usual way by converting the active agents with suitable additives, vehicles, and flavor ameliorating substances into the desired forms of administration, such as tablets, dragees, capsules, solutions, inhalants, etc.

The pharmacologically active compounds of this invention can be processed in accordance with conventional methods of galenic pharmacy to produce medicinal agents for administration to patients, e.g., mammals, including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and-/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The dosage of the compounds according to this invention generally is 1–20 mg/kg/day when administered to patients, e.g., humans as an antiinflammatory, analogously to the known agent indomethacin. Suitable dosages and administration regimens for a given host can be determined using conventional considerations, e.g., by customary comparison of the differential activities of the subject compound and of a known agent e.g., indomethacin, by means of an appropriate, conventional pharmacological protocol such as those mentioned above.

Especially suitable for oral administration are tablets, dragees, and capsules, which contain, for example, 1–250 mg of active ingredient and 50 mg to 2 g of a pharmacologically inert carrier, such as, for example, lactose, amylose, talc, gelatin, magnesium stearate, and similar materials, as well as the customary additives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

3.12 g of 4,5-bis(4-methoxyphenyl)-2-mercaptoimidazole is dissolved in 50 ml of absolute dimethylformamide and combined with 0.3 g of sodium hydride (80% strength in white oil). The mixture is agitated for 30 minutes, and then 2.31 g of 2-iodothiophene in 25 ml of dimethylformamide is added dropwise thereto. The reaction mixture is combined with one pinch of powdered copper and agitated for 12 hours under argon at 100°. The solution is then poured into 300 ml of ice water, the product extracted with ethyl acetate, the organic solution dried over sodium sulfate, and concentrated to dryness under vacuum. The residue is chromatographed on 200 g of silica gel. With acetone/hexane 2:3, 3.06 g of 4,5-bis(4-methoxyphenyl)-2-(2-thienylthio)imidazole is eluted, exhibiting a melting point of 156° after recrystallization from diisopropyl ether.

EXAMPLE 2

3.12 g of 4,5-bis(4-methoxyphenyl)-2-mercaptoimidazole is dissolved in 50 ml of absolute dimethylformamide and combined with 0.3 g of sodium hydride (80% strength in white oil). The mixture is stirred for 30 minutes, and then 1.74 g of 2-bromopyridine in 25 ml of dimethylformamide is added dropwise thereto. The reaction mixture is stirred at room temperature under argon for 30 hours. Then the solution is poured into 300 ml of ice water, the product is extracted with ethyl acetate, the organic solution is dried over sodium sulfate and concentrated to dryness under vacuum. The residue is recrystallized from methylene chloride/ether, thus obtaining 2.94 g of 4,5-bis(4-methoxyphenyl)-2-(2-pyridylthio)imidazole, mp 94°.

EXAMPLE 3

3.12 g of 4,5-bis(4-methoxyphenyl)-2-mercaptoimidazole is dissolved in 50 ml of absolute dimethylformamide and combined with 0.3 g of sodium hydride (80% strength in white oil). The mixture is agitated for 30 minutes and then 1.81 g of 2-bromothiazole in 25 ml of dimethylformamide is added dropwise thereto. The reaction mixture is combined with a pinch of powdered copper and stirred for 6 hours under argon at 80°. The solution is then poured into 300 ml of ice water, the product is extracted with ethyl acetate, the organic solution is dried over sodium sulfate and concentrated to dryness under vacuum. The residue is chromatographed on 200 g of silica gel. With acetone/hexane, 3.14 g of 4,5-bis(4-methoxyphenyl)-2-(2-thiazolylthio)imidazole is eluted which has a melting point of 145° after recrystallization from diisopropyl ether.

EXAMPLE 4

3.12 g of 4,5-bis(4-methoxyphenyl)-2-mercaptoimidazole is dissolved in 50 ml of absolute dimethylformamide and combined with 0.3 g of sodium hydride (80% strength in white oil). The mixture is stirred for 30 minutes and then 1.26 g of 2-chloropyrimidine in 25 ml of dimethylformamide is added dropwise thereto. The reaction mixture is combined with a pinch of powdered copper and stirred for one week under argon at room temperature. The solution is then poured into 300 ml of ice water, the product is extracted with ethyl acetate, the organic solution is dried over sodium sulfate and concentrated to dryness under vacuum. The residue is recrystallized from glacial acetic acid/ether, thus obtaining 2.87 g of 4,5-bis(4-methoxyphenyl)-2-(2-pyrimidylthio)imidazole, mp 86°.

EXAMPLE 5

3.12 g of 4,5-bis(4-methoxyphenyl)-2-mercaptoimidazole is dissolved in 50 ml of absolute dimethylformamide and combined with 0.3 g of sodium hydride (80% strength in white oil). The reaction mixture is agitated for 30 minutes and then 2.61 g of 2-iodonitrobenzene in 25 ml of dimethylformamide is added dropwise to the reaction mixture, and the latter is stirred for 16 hours under argon at room temperature, then poured into 300 ml of ice water, the product is extracted with ethyl acetate, the organic solution is dried over sodium sulfate and concentrated to dryness under vacuum. The residue is chromatographed on 200 g of silica gel. With acetone/hexane 2:3, 3.35 g of 4,5-bis(4-methoxyphenyl)-2-(2-nitrophenylthio)imidazole is eluted which has a melting point of 127°–129° after recrystallization from diisopropyl ether.

EXAMPLE 6

At room temperature, 2.5 g of iron filings is added to a solution of 4.34 g of 4,5-bis(4-methoxyphenyl)-2-(2-nitrophenylthio)imidazole in 50 ml of glacial acetic acid and 3 ml of acetic anhydride. The mixture is stirred overnight, poured into 500 ml of water, the precipitated product is vacuum-filtered, taken up in ethyl acetate, and the solution washed with sodium bicarbonate solution. The solution is then dried over sodium sulfate and concentrated to dryness under vacuum. The residue is crystallized from ethyl acetate/ether. Recrystallization from ethyl acetate yields 3.67 g of 4,5-bis(4-methoxyphenyl)-2-(2-acetamidophenylthio)imidazole, mp 183°.

EXAMPLE 7

Under agitation and a layer of argon, a solution of 3.77 g of 4-chloro-3-nitrotrifluoromethylbenzene in 50 ml of dimethylformamide is added dropwise to a solution of 4.82 g of 4,5-bis(4-chlorophenyl)-2-mercaptoimidazole and 0.45 g of sodium hydride (80% strength in white oil) in 100 ml of dimethylformamide. The mixture is stirred for 20 minutes, concentrated under vacuum, and the residue is distributed between water and ethyl acetate. The organic solution is dried over sodium sulfate and concentrated to dryness under vacuum. The residue is crystallized from methylene chloride/ether, thus obtaining 6.82 g of 4,5-bis(4-chlorophenyl)-2-(2-nitro-4-trifluoromethylphenylthio)imidazole, mp 264°–266°.

EXAMPLE 8

Under stirring and a layer of argon, a solution of 7.45 g of 4-chloro-3-nitrotrifluoromethylbenzene in 40 ml of dimethylformamide is added dropwise to a solution of 7.94 g of 4,5-diphenyl-2-mercaptoimidazole and 0.45 g of sodium hydride (80% strength in white oil) in 150 ml of dimethylformamide. The mixture is agitated for 20 minutes, concentrated under vacuum, and the residue distributed between water and ethyl acetate. The organic solution is dried over sodium sulfate and concentrated to dryness under vacuum. The residue is crystallized from ether, thus obtaining 11.87 g of 4,5-diphenyl-2-(2-nitro-4-trifluoromethylphenylthio)imidazole, mp 234°–236°.

EXAMPLE 9

At 60° under thorough agitation, 4.2 g of sodium dithionite (about 87% strength) is added to a solution of 4.41 g of 4,5-diphenyl-2-(2-nitro-4-trifluoromethylphenylthio)imidazole in a mixture of 100 ml of dioxane, 48 ml of water, and 2 ml of concentrated ammonia. The color of the solution changes over from reddish brown to pale yellow. The mixture is poured into 700 ml of ice water, extracted with ethyl acetate, the organic solution is dried over sodium sulfate, and concentrated to dryness under vacuum. The residue is dissolved in ethanol and combined with 10 ml of ethereal hydrochloric acid. The product commences crystallization during concentration. After recrystallization from ethanol, 3.89 g of 4,5-diphenyl-2-(2-amino-4-trifluoromethylphenylthio)imidazole hydrochloride is obtained having a decomposition point of 177°–179°.

EXAMPLE 10

2.24 g of 4,5-diphenyl-2-(2-amino-4-trifluoromethylphenylthio)imidazole hydrochloride is dissolved in 100 ml of methanolic hydrochloric acid and combined at 0° with 0.586 g of isoamyl nitrite. The mixture is agitated for 30 minutes, then heated to boiling for 2 hours and the solution evaporated under vacuum to dryness. The residue is distributed between ethyl acetate and sodium bicarbonate solution. The organic solution is dried over sodium sulfate and concentrated to dryness under vacuum. The residue is crystallized from ether/chloroform, thus obtaining 1.61 g of 4,5-diphenyl-2-(4-trifluoromethylphenylthio)imidazole, mp 227°–229°.

EXAMPLE 11

Under agitation and covering with argon, a solution of 4.52 g of 4-chloro-3-nitrotrifluoromethylbenzene in 25 ml of dimethylformamide is added dropwise to a solution of 5.61 g of 4,5-bis(4-methylphenyl)-2-mercaptoimidazole and 0.6 g of sodium hydride (80% strength in white oil) in 200 ml of dimethylformamide. The solution is further stirred for 30 minutes, concentrated under vacuum, and the residue distributed between water and ethyl acetate. The organic solution is dried over sodium sulfate and concentrated to dryness under vacuum. The residue is crystallized from ethanol, thus producing 8.26 g of 4,5-bis(4-methylphenyl)-2-(2-nitro-4-trifluoromethylphenylthio)imidazole in fine yellow needles having a decomposition point of 252°.

EXAMPLE 12

Under agitation and a layer of argon, a solution of 4.52 g of 4-chloro-3-nitrotrifluoromethylbenzene in 25 ml of dimethylformamide is added dropwise to a solution of 6.25 g of 4,5-bis(4-methoxyphenyl)-2-mercaptoimidazole and 0.6 g of sodium hydride (80% strength in white oil) in 200 ml of dimethylformamide. The solution is further stirred for 20 minutes, concentrated under vacuum, and the residue distributed between water and ethyl acetate. The organic solution is dried over sodium sulfate and concentrated to dryness under vacuum. The residue is crystallized from hexane/acetone, thus obtaining 9.44 g of 4,5-bis(4-methoxyphenyl)-2-(2-nitro-4-trifluoromethylphenylthio)imidazole in yellow needles, mp 264°–266°.

EXAMPLE 13

At 60° under thorough agitation, 8.5 g of sodium dithionite (about 87% strength) is added to a solution of 10.3 g of 4,5-bis(4-methoxyphenyl)-2-(2-nitro-4-trifluoromethylphenylthio)imidazole in a mixture of 300 ml of dioxane, 95 ml of water, and 5 ml of concentrated ammonia. The color of the solution changes over from reddish brown to pale yellow. The reaction mixture is poured into 1 liter of ice water, extracted with ethyl acetate, the organic solution dried over sodium sulfate, concentrated to dryness under vacuum, and the residue is dissolved in ethanol and combined with 10 ml of ethereal hydrochloric acid. The product begins to crystallize during concentration. After recrystallization from ethanol, 8.28 g of 4,5-bis(4-methoxyphenyl)-2-(2-amino-4-trifluoromethylphenylthio)imidazole hydrochloride is obtained, decomposition point 200°–202°.

EXAMPLE 14

2.61 g of 4,5-bis(4-methoxyphenyl)-2-(2-amino-4-trifluoromethylphenylthio)imidazole hydrochloride is suspended in a mixture of 70 ml of absolute ethanol, 30 ml of absolute dioxane, and 365 mg of hydrochloric acid and combined at 0° with 0.586 g of isoamyl nitrite. The mixture is agitated for 30 minutes, then heated for 2 hours to boiling, and the solution evaporated to dryness under vacuum. The residue is distributed between ethyl acetate and sodium bicarbonate solution. The organic solution is dried over sodium sulfate and concentrated to dryness under vacuum. The residue is crystallized from ether/methylene chloride, thus obtaining 2.01 g of 4,5-bis(4-methoxyphenyl)-2-(4-trifluoromethylphenylthio)imidazole, mp 184°–186°.

EXAMPLE 15

1.5 g of aniline is dissolved in 2.0 g of concentrated sulfuric acid and 30 ml of water and, after the addition of 10 g of ice, diazotized at 0° with a solution of 1.2 g of sodium nitrite in 10 ml of water. The diazonium salt solution is then neutralized with sodium acetate and introduced at 5° under thorough agitation into a solution of 5.02 g of 4,5-bis(4-methoxyphenyl)-2-mercaptoimidazole in 200 ml of dimethylformamide containing 10 ml of water, 1.93 g of sodium hydroxide solution, as well as 1.15 g of powdered copper. The mixture is further stirred for 20 minutes, poured into 600 ml of water, the thus-precipitated oil is taken up in methylene chloride, the organic solution is washed with water, dried over sodium sulfate, and concentrated to dryness under vacuum. The residue is chromatographed on 200 g of silica gel. Elution with acetone/hexane 2:3 yields 2.47 g of 4,5-bis(4-methoxy-phenyl)-2-(phenylthio)imidazole, mp 177°–179° after recrystallization from hexane/ethyl acetate.

EXAMPLE 16

At 0° a diazonium salt solution prepared from 2.5 g of 2-fluoroaniline, 1.58 g of sodium nitrite, and 10 ml of 6N hydrochloric acid is added dropwise to a solution of 6.25 g of 4,5-bis(4-methoxyphenyl)-2-mercaptoimidazole in a mixture of 240 ml of dimethylformamide, 10 ml of 2N sodium hydroxide solution, and 1.45 g of powdered copper. The solution develops a reddish brown color under nitrogen evolution. The mixture is further stirred for 3 hours, concentrated under vacuum, and the residue is distributed between water and ethyl acetate. The organic solution is dried over sodium sulfate and concentrated to dryness under vacuum. The residue is subjected to column chromatography on 500 g of silica gel. Elution with acetone/hexane 2:3 yields 2.71 g of 4,5-bis(4-methoxyphenyl)-2-(2-fluorophenylthio)imidazole having a melting point of 195° after recrystallization from hot diisopropyl ether.

EXAMPLE 17

At 0° a diazonium salt solution prepared from 2.5 g of 4-fluoroaniline, 1.58 g of sodium nitrite, and 10 ml of 6N hydrochloric acid is added dropwise to a solution of 6.25 g of 4,5-bis(4-methoxyphenyl)-2-mercaptoimidazole in a mixture of 240 ml of dimethylformamide, 10 ml of 2N sodium hydroxide solution, and 1.45 g of pulverized copper. The solution assumes a reddish brown color under evolution of nitrogen. The mixture is agitated for another 3 hours, the solution is concentrated under vacuum, and the residue is distributed between water and ethyl acetate. The organic solution is dried over sodium sulfate and concentrated to dryness under vacuum. The residue is chromatographed over a column on 500 g of silica gel. Elution with acetone/hexane 2:3 yields 3.09 g of 4,5-bis(4-methoxyphenyl)-2-(4-fluorophenylthio)imidazole, mp 106° after recrystallization from hot diisopropyl ether/methylene chloride.

EXAMPLE 18

At 0° a diazonium salt solution prepared from 2.58 g of 2,4-difluoroaniline, 1.58 g of sodium nitrite, and 10 ml of 6N hydrochloric acid is added dropwise to a solution of 6.25 g of 4,5-bis(4-methoxyphenyl)-2-mercaptoimidazole in a mixture of 240 ml of dimethylformamide, 10 ml of 2N sodium hydroxide solution, and 1.45 g of powdered copper. The solution becomes reddish brown under nitrogen evolution. The mixture is stirred for another 3 hours, the solution is concentrated under vacuum, and the residue is distributed between water and ethyl acetate. The organic solution is dried over sodium sulfate and concentrated to dryness under vacuum. The residue is subjected to column chromatography on 500 g of neutral aluminum oxide (activity stage II). Elution with acetone/hexan 2:3 yields 3.12 g of 4,5-bis(4-methoxyphenyl)-2-(2,4-difluorophenylthio)imidazole, having a melting point of 174°–176° after crystallization from hexane/ether and a melting point of 186°–188° after another crystallization from ethanol/ether.

EXAMPLE 19

5.49 g of 3-fluoroaniline is dissolved in 6.0 g of concentrated sulfuric acid and 120 ml of water and, after the addition of 10 g of ice, diazotized at 0° with a solution of 3.6 g of sodium nitrite in 10 ml of water. The diazonium salt solution is then neutralized with sodium acetate and introduced at 5° under thorough agitation into a solution of 17.2 g of 4,5-bis(4-methoxyphenyl)-2-mercaptoimidazole in 700 ml of dimethylformamide. The mixture is agitated for another 20 minutes, poured into 2.5 l of water, extracted with ethyl acetate, the organic solution washed with water, dried over sodium sulfate, and concentrated to dryness under vacuum. The residue is chromatographed on 500 g of neutral aluminum oxide (activity stage II). Elution with ethyl acetate/hexane produces 7.24 g of 4,5-bis(4-methoxyphenyl)-2-(3-fluorophenylthio)imidazole, mp 147°–149° after recrystallization from ether/ethyl acetate.

EXAMPLE 20

Under argon and with agitation, 17.5 ml of 1.5N n-butyllithium in hexane, diluted with 20 ml of benzene, is added dropwise at 0° to a solution of 8.11 g of 4,5-bis(4-methoxyphenyl)-1-methoxymethylimidazole in a mixture of 50 ml of absolute ether and 50 ml of benzene. After 20 minutes, a solution of 5.45 g of diphenyldisulfide in 25 ml of absolute ether is added dropwise thereto; during this step, the temperature does not exceed 20°. After 2 hours of agitation at room temperature, the solution is extracted with 2N sodium hydroxide solution. The organic solution is concentrated to dryness under vacuum. From hexane/benzene, 8.01 g of 4,5-bis(4-methoxyphenyl)-1-methoxymethyl-2-phenylthioimidazole is crystallized, mp 88°–90°.

The compound is dissolved in 50 ml of glacial acetic acid, combined with 10 ml of 6N hydrochloric acid, and refluxed for 6 hours. The solvent is then removed under vacuum, and the residue is distributed between sodium bicarbonate solution and ethyl acetate. The organic solution is dried over sodium sulfate, concentrated to dryness under vacuum, the residue is crystallized from hexane/ethyl acetate, and the product is 6.27 g of 4,5-bis(4-methoxyphenyl)-2-phenylthioimidazole, mp 177°–179°.

Production of 4,5-bis(4-methoxyphenyl)-1-methoxymethylimidazole:

Incremental portions of 3.6 g of sodium hydride (50% strength in white oil) is added to a solution of 21 g of 4,5-bis(4-methoxyphenyl)imidazole in 75 ml of absolute dimethylformamide. The mixture is stirred for another 30 minutes, and then 6.3 ml of 1-chloromethylmethyl ether in 35 ml of dimethylformamide is added dropwise. After 30 minutes the mixture is poured on ice water, the product is taken up in chloroform, the organic solution is washed with water, dried over sodium sulfate, and concentrated to dryness under vacuum. The residue is crystallized from benzene/hexane, thus obtaining 18.31 g of 4,5-bis(4-methoxyphenyl)-1-methoxymethylimidazole, mp 99°–101°.

EXAMPLE 21

Under agitation and with argon as a protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes, a solution of 3.31 g of 4,4'-di-tert-butyldiphenyldisulfide in 25 ml of absolute ether is added thereto, the temperature being maintained at between −5° and 0° by cooling. After 6 hours of agitation at room temperature, the mixture is poured into 800 ml of water, the product is allowed to crystallize and is vacuum-filtered, taken up in ether, the solution dried over sodium sulfate, and concentrated until onset of crystallization. After recrystallization from ether/hexane, 3.69 g of 4,5-bis(4-methoxyphenyl)-2-(4-tert-butylphenylthio)-1-(tetrahydropyran-2-yl)imidazole is obtained, mp 162°–164°.

The compound is taken up in 25 ml of ethanol, combined with 2 ml of 6N hydrochloric acid, and heated for 10 minutes on a water bath. The solvent is then removed under vacuum and the residue crystallized from ethanol/ether, thus obtaining 3.08 g of 4,5-bis(4-methoxyphenyl)-2-(4-tert-butylphenylthio)imidazole, mp 172°–174°.

Production of 4,5-bis(4-methoxyphenyl)-1-tetrahydropyran-2-yl)imidazole:

14.17 g of 4,5-bis(4-methoxyphenyl)imidazole is suspended in 250 ml of absolute 1,2-dichloroethane and combined with 16 g of 3,4-dihydro-2H-pyran as well as 0.5 ml of tin tetrachloride. The mixture is heated to reflux under agitation for 12 hours, then allowed to cool, and poured into 500 ml of cold sodium bicarbonate solution. The organic phase is separated, dried over sodium sulfate, and concentrated under vacuum. The residue is dissolved in dichloromethane and subjected to hexane precipitation. The sediment is dissolved in ether. The solution is clarified with activated carbon, concentrated under vacuum, and made to crystallize, thus producing 15.03 g of 4,5-bis(4-methoxyphenyl)-1-(tetrahydropyran-2-yl)imidazole, mp 127°–128°.

EXAMPLE 22

Under agitation and with argon as a protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes a solution of 3.56 g of 3,3′,4,4′-tetrachlorodiphenyldisulfide in 30 ml of absolute ether is added dropwise to the reaction mixture, while maintaining the temperature by cooling at between −5° and 0°. After 6 hours of stirring at room temperature, the mixture is poured into 800 ml of water, the product is allowed to crystallize and vacuum-filtered, taken up in ether, the solution dried over sodium sulfate and concentrated until the onset of crystallization. Recrystallization from ether/chloroform yields 4.68 g of 4,5-bis(4-methoxyphenyl)-2-(3,4-dichlorophenylthio)-1-(tetrahydropyran-2-yl)imidazole, mp 125°–127°.

The compound is taken up in 25 ml of ethanol, combined with 5 ml of ethereal hydrochloric acid, and heated for 10 minutes on a water bath. The solvent is then withdrawn under vacuum and the residue distributed between ethyl acetate and aqueous sodium bicarbonate solution; the organic phase is dried over sodium sulfate, concentrated to dryness under vacuum, and the residue crystallized from ethanol/ether, thus obtaining 3.41 g of 4,5-bis(4-methoxyphenyl)-2-(3,4-dichlorophenylthio)imidazole, mp 113°–115°.

EXAMPLE 23

Under agitation and with argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes a solution of 3.76 g of 4,4′-dibromodiphenyldisulfide in 300 ml of absolute ether is added dropwise to the mixture, while maintaining the temperature at between −5° and 0° by cooling. After 6 hours of agitation at room temperature, the mixture is poured into 800 ml of water, the product is allowed to crystallize and vacuum-filtered. The product is then taken up in ether, the solution is dried over sodium sulfate and concentrated until incipient crystallization. Recrystallization from ether/chloroform yields 4.27 g of 4,5-bis(4-methoxyphenyl)-2-(3,4-dichlorophenylthio)-1-(tetrahydropyran-2-yl)imidazole, mp 192°–194°.

The compound is taken up in 25 ml of ethanol, combined with 5 ml of ethereal hydrochloric acid, and heated for 10 minutes on a water bath. The solvent is then removed under vacuum and the residue distributed between ethyl acetate and aqueous sodium bicarbonate solution, the organic phase is dried over sodium sulfate, concentrated to dryness under vacuum, and the residue crystallized from ethanol/ether, yielding 3.19 g of 4,5-bis(4-methoxyphenyl)-2-(3,4-dichlorophenylthio)imidazole, mp 138°–140°.

EXAMPLE 24

Under agitation and using argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes a solution of 2.87 g of 4,4′-dichlorodiphenyldisulfide in 50 ml of absolute ether is added dropwise to the reaction mixture, maintaining the temperature at between −5° and 0° by cooling. After 6 hours of agitation at room temperature, the mixture is poured into 800 ml of water, the product is allowed to crystallize and vacuum-filtered. The product is then taken up in ether, the solution is dried over sodium sulfate and concentrated to onset of crystallization. Recrystallization from ether/chloroform yields 4.68 g of 4,5-bis(4-methoxyphenyl)-2-(4-chlorophenylthio)-1-(tetrahydropyran-2-yl)imidazole, mp 202°–204°.

The compound is taken up in 25 ml of ethanol, combined with 5 ml of ethereal hydrochloric acid, and heated for 10 minutes on a water bath. The solvent is then removed under vacuum and the residue distributed between ethyl acetate and aqueous sodium bicarbonate solution; the organic phase is dried over sodium sulfate, concentrated to dryness under vacuum, and the residue crystallized from ethanol/ether, thus obtaining 3.41 g of 4,5-bis(4-methoxyphenyl)-2-(4-chlorophenylthio)imidazole, mp 148°–150°.

EXAMPLE 25

Under stirring and the use of argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes, a solution of 2.71 g of 4,4′-dimethyldiphenyldisulfide in 50 ml of absolute ether is added dropwise to the reaction mixture while maintaining the temperature by cooling between −5° and 0°. After 6 hours of agitation at room temperature, the mixture is poured into 800 ml of water, the product is taken up in ethyl acetate, the organic solution is dried over sodium sulfate and concentrated to dryness under vacuum. The residue is purified by chromatography on silica gel with hexane/acetone 3:2. Recrystallization from ether yields 3.97 g of 4,5-bis(4-methoxyphenyl)-2-(4-methylphenylthio)-1-(tetrahydropyran-2-yl)imidazole, mp 192°.

The compound is taken up in 25 ml of ethanol, combined with 5 ml of ethereal hydrochloric acid, and heated for 10 minutes on a water bath. The solvent is thereafter removed under vacuum, the residue distributed between ethyl acetate and aqueous sodium bicarbonate solution, the organic phase is dried over sodium sulfate, concentrated to dryness under vacuum, and the residue crystallized from ethanol/ether, yielding 4,5-bis(4-methoxyphenyl)-2-(4-methylphenylthio)imidazole, mp 181°.

EXAMPLE 26

Under stirring and with argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes, a solution of 2.87 g of 4,4′-dimethoxydiphenyldisulfide in 40 ml of absolute ether is added dropwise to the mixture while maintaining the temperature between −5° and 0° by cooling. After 6 hours of stirring at room temperature, the mixture is poured into 800 ml of water, the product is taken up in ethyl acetate, the organic solution is dried over sodium sulfate and concentrated to dryness under vacuum. The residue is purified by chromatography on silica gel with hexane/acetone 3:2. Recrystallization from ether results in 4.27 g of 4,5-bis(4-methoxyphenyl)-2-(4-methoxyphenylthio)-1-(tetrahydropyran-2-yl)imidazole, mp 152°.

The compound is taken up in 25 ml of ethanol, combined with 5 ml of ethereal hydrochloric acid, and heated for 10 minutes on a water bath. The solvent is then withdrawn under vacuum, the residue is distributed between ethyl acetate and aqueous sodium bicarbonate solution, the organic phase is dried over sodium sulfate, concentrated to dryness under vacuum, and the residue is crystallized from ether, thus obtaining 3.10 g of 4,5-bis(4-methoxyphenyl)-2-(4-methoxyphenylthio)imidazole, mp 148°.

EXAMPLE 27

Under agitation and with argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes, a solution of 2.87 g of 2,2'-dimethoxydiphenyldisulfide in 50 ml of absolute ether is added dropwise to the reaction mixture while maintaining the temperature at between −5° and 0° by cooling. After 6 hours of agitation at room temperature, the mixture is poured into 800 ml of water, the product is taken up in ethyl acetate, the organic solution is dried over sodium sulfate and concentrated to dryness under vacuum. The residue is purified by chromatography on silica gel with hexane/acetone 3:2. Recrystallization from ether yields 4.13 g of 4,5-bis(4-methoxyphenyl)-2-(2-methoxyphenylthio)-1-tetrahydropyran-2-yl)imidazole, mp 166°.

The compound is taken up in 25 ml of ethanol, combined with 5 ml of ethereal hydrochloric acid, and heated for 10 minutes on a water bath. The solvent is then removed under vacuum, and the residue is crystallized from toluene/petroleum ether, thus obtaining 2.93 g of 4,5-bis(4-methoxyphenyl)-2-(2-methoxyphenylthio)imidazole, mp 161°.

EXAMPLE 28

Under stirring and with argon as the protective gas, 7 ml of approximately 1.5N n-butyllithium in hexane, diluted with 10 ml of benzene, is added dropwise at −5° to 0° to a solution of 3.65 g of 4,5-bis(4-methoxyphenyl)-1-(2-tetrahydropyran-2-yl)imidazole in a mixture of 50 ml of absolute ether and 50 ml of benzene. After 20 minutes, a solution of 2.87 g of 3,3'-dimethoxydiphenyldisulfide in 30 ml of absolute ether is added dropwise to the reaction mixture, while the temperature is maintained by cooling between −5° and 0°. After 6 hours of agitation at room temperature, the mixture is poured into 800 ml of water, the product is taken up in ethyl acetate, the organic solution is dried over sodium sulfate and concentrated to dryness under vacuum. The residue is purified by chromatography on silica gel with hexane/acetone 3:2. Recrystallization from ether produces 3.90 g of 4,5-bis(4-methoxyphenyl)-2-(3-methoxyphenylthio)-1-(tetrahydropyran-2-yl)imidazole, mp 123°.

The compound is taken up in 25 ml of ethanol, combined with 5 ml of ethereal hydrochloric acid, and heated for 10 minutes on a water bath. The solvent is then removed under vacuum and the residue distributed between ethyl acetate and aqueous sodium bicarbonate solution; the organic phase is dried over sodium sulfate, concentrated to dryness under vacuum, and the residue crystallized from ethanol/ether, thus obtaining 3.08 g of 4,5-bis(4-methoxyphenyl)-2-(3-methoxyphenylthio)imidazole, mp 101°.

EXAMPLE 29

Under agitation and a layer of argon, 34.5 ml of an approximately 1.6N solution of butyllithium in hexane is added dropwise under cooling to a suspension of 14.7 g of 4,5-bis(4-methoxyphenyl)-1-methylimidazole in 150 ml of a mixture of absolute ether/benzene 2:1, thus dissolving the solid matter. The mixture is agitated for another 30 minutes and then 10.9 g of diphenyldisulfide dissolved in 50 ml of absolute ether is added dropwise thereto; during this step, the temperature is not allowed to rise above 40° by cooling the mixture. After another 30 minutes of agitation, the solution is washed with 2N sodium hydroxide solution and water, dried over sodium sulfate, and concentrated to dryness under vacuum. The residue is crystallized from ether, thus obtaining 17.4 g of 4,5-bis(4-methoxyphenyl)-2-phenylthio-1-methylimidazole, mp 115°–117°.

Preparation of 4,5-bis(4-methoxyphenyl)-1-methylimidazole:

1.8 g of sodium hydride (50% in white oil) is added in incremental portions to a solution of 10.5 g of 4,5-bis(4-methoxyphenyl)imidazole in 50 ml of absolute dimethylformamide. The mixture is agitated for another 30 minutes and then 5.35 g of methyl iodide in 50 ml of dimethylformamide is dropped thereto. After 60 minutes, the mixture is poured into ice water, the product taken up in ethyl acetate, the organic solution dried over sodium sulfate and concentrated under vacuum. The residue is recrystallized from benzene, thus obtaining 9.59 g of 4,5-bis(4-methoxyphenyl)-1-methylimidazole, mp 122°–123°.

EXAMPLE 30

A suspension of 7.4 g of 4,5-bis(4-methoxyphenyl)-1-benzylimidazole in 100 ml of a mixture of absolute ether/benzene 1:1 is combined dropwise under cooling with 13.8 ml of an approximately 1.6N solution of butyllithium in hexane under agitation and a layer of argon; the temperature does not rise above 20° by cooling the mixture. The latter is then stirred for another 30 minutes and then 4.36 g of diphenyldisulfide in 25 ml of absolute ether is added as a solution to the reaction mixture. After 30 minutes of further agitation, the solution is washed with 2N sodium hydroxide and water, dried over sodium sulfate, and concentrated to dryness under vacuum. The residue is crystallized from methylene chloride/ether, thus obtaining 8.53 g of 4,5-bis(4-methoxyphenyl)-2-phenylthio-1-benzylimidazole, mp 113°–115°.

Production of 4,5-bis(4-methoxyphenyl)-1-benzylimidazole:

Incremental portions of 1.8 g of sodium hydride (50% strength in white oil) is added to a solution of 10.5 g of 4,5-bis(4-methoxyphenyl)imidazole in 50 ml of absolute dimethylformamide. The mixture is agitated for 30 minutes and then 6.75 g of benzyl bromide in 50 ml of dimethylformamide is added dropwise thereto. After 30 minutes, the mixture is poured on ice water, the product is taken up in ethyl acetate, the organic solution dried over sodium sulfate and concentrated to dryness under vacuum. The residue is recrystallized from ethanol, thus obtaining 13.89 g of 4,5-bis(4-methoxyphenyl)-1-benzylimidazole, mp 165°–167°.

EXAMPLE 31

A solution of 2.164 g of 3-chloroperbenzoic acid (80%) in 150 ml of dichloromethane is added dropwise to a solution of 3.89 g of 4,5-bis(4-methoxyphenyl)-2-phenylthioimidazole in 100 ml of dichloromethane. The mixture is stirred for 3 hours at room temperature, the solution is washed with sodium bicarbonate solution, dried over sodium sulfate, and concentrated to dryness under vacuum. The residue is crystallized from ether/hexane. Recrystallization from ether/hexane yields 3.36 g of 4,5-bis(4-methoxyphenyl)-2-phenylsulfinylimidazole, mp 188°–190°.

EXAMPLE 32

A solution of 4.33 g of 3-chloroperbenzoic acid (80%) in 300 ml of dichloromethane is added dropwise to a solution of 3.89 g of 4,5-bis(4-methoxyphenyl)-2-phenylthioimidazole in 100 ml of dichloromethane. The mixture is stirred for 3 hours at room temperature, the solution is washed with sodium bicarbonate solution, dried over sodium sulfate, and concentrated to dryness under vacuum. The residue is crystallized from ether/methylene chloride, thus obtaining 3.27 g of 4,5-bis(4-methoxyphenyl)-2-phenylsulfonylimidazole, mp 106°.

EXAMPLE 33

A solution of 2.164 g of 3-chloroperbenzoic acid (80%) in 150 ml of dichloromethane is added dropwise to a solution of 3.95 g of 4,5-bis(4-methoxyphenyl)-2-(2-thienylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus producing 3.47 g of 4,5-bis(4-methoxyphenyl)-2-(2-thienylsulfinyl)imidazole as an amorphous foam.

$C_{21}H_{18}N_2O_3S_2$ (410.52): Calculated: 61.44% C, 4.20% H, 6.82% N, 15.62% S. Found: 61.27% C, 4.29% H, 6.71% N, 15.50% S.

EXAMPLE 34

A solution of 4.33 g of 3-chloroperbenzoic acid (80%) in 300 ml of dichloromethane is added dropwise to a solution of 3.95 g of 4,5-bis(4-methoxyphenyl)-2-(2-thienylthio)imidazole in 100 ml of dichloromethane. The solution is agitated for 3 hours at room temperature, washed with sodium bicarbonate solution, dried over sodium sulfate, and concentrated to dryness under vacuum. The residue is crystallized from ether, thus obtaining 3.19 g of 4,5-bis(4-methoxyphenyl)-2-(2-thienylsulfonyl)imidazole, mp 179°.

EXAMPLE 35

A solution of 2.164 g of 3-chloroperbenzoic acid (80%) in 150 ml of dichloromethane is added dropwise to a solution of 3.95 g of 4,5-bis(4-methoxyphenyl)-2-(2-thiazolylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane 2:3, thus obtaining 3.28 g of 4,5-bis(4-methoxyphenyl)-2-(2-thiazolylsulfinyl)imidazole as an amorphous foam.

$C_{20}H_{17}N_3O_3S_2$ (411.50): Calculated: 58.38% C, 4.16% H, 10.21% N, 15.58% S. Found: 58.24% C, 4.37% H, 10.13% N, 15.49% S.

EXAMPLE 36

A solution of 4.33 g of 3-chloroperbenzoic acid (80%) in 300 ml of dichloromethane is added dropwise to a solution of 3.96 g of 4,5-bis(4-methoxyphenyl)-2-(2-thiazolylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.39 g of 4,5-bis(4-methoxyphenyl)-2-(2-thiazolylsulfonyl)imidazole, mp 219°.

EXAMPLE 37

A solution of 2.164 g of 3-chloroperbenzoic acid (80%) in 150 ml of dichloromethane is added dropwise to a solution of 4.57 g of 4,5-bis(4-methoxyphenyl)-2-(3,4-dichlorophenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane 2:3, thus obtaining 4.19 g of 4,5-bis(4-methoxyphenyl)-2-(3,4-dichlorophenylsulfinyl)imidazole as an amorphous foam.

$C_{23}H_{18}Cl_2N_2O_3S$ (473.38): Calculated: 58.35% C, 3.83% H, 14.98% Cl, 5.92% N, 6.77% S. Found: 58.30% C, 3.91% H, 14.88% Cl, 5.84% N, 6.66% S.

EXAMPLE 38

A solution of 2.164 g of 3-chloroperbenzoic acid (80%) in 150 ml of dichloromethane is added dropwise to a solution of 4.26 g of 4,5-bis(4-methoxyphenyl)-2-(3,4-dichlorophenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane and the product is 4.19 g of 4,5-bis(4-methoxyphenyl)-2-(3,4-dichlorophenylsulfonyl)imidazole as an amorphous foam.

$C_{23}H_{18}Cl_2N_2O_4S$ (489.38): Calculated: 56.45% C, 3.71% H, 14.49% Cl, 5.72% N, 6.55% S. Found: 56.29% C, 3.82% H, 14.40% Cl, 5.67% N, 6.48% S.

EXAMPLE 39

A solution of 2.164 g of 3-chloroperbenzoic acid (80%) in 150 ml of dichloromethane is dropped to a solution of 4.07 g of 4,5-bis(4-methoxyphenyl)-2-(4-fluorophenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.86 g of 4,5-bis(4-methoxyphenyl)-2-(4-fluorophenylsulfinyl)imidazole as an amorphous foam.

$C_{23}H_{19}FN_2O_3S$ (422.49): Calculated: 65.39% C, 4.53% H, 4.50% F, 6.63% N, 7.59% S. Found: 65.27% C, 4.65% H, 4.44% F, 6.54% N, 7.48% S.

EXAMPLE 40

A solution of 4.33 g of 3-chloroperbenzoic acid (80%) in 300 ml of dichloromethane is added dropwise to a solution of 4.07 g of 4,5-bis(4-methoxyphenyl)-2-(4-fluorophenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, thus producing 3.98 g of 4,5-bis(4-methoxyphenyl)-2-(4-fluorophenylsulfonyl)imidazole as an amorphous foam.

$C_{23}H_{19}FN_2O_4S$ (438.49): Calculated: 63.00% C, 4.37% H, 4.33% F, 6.39% N, 7.31% S. Found: 63.13% C, 4.46% H, 4.29% F, 6.33% N, 7.24% S.

EXAMPLE 41

A solution of 2.164 g of 3-chloroperbenzoic acid (80%) in 150 ml of dichloromethane is added dropwise to a solution of 4.07 g of 4,5-bis(4-methoxyphenyl)-2-(3-fluorophenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, yielding 3.04 g of 4,5-bis(4-methoxyphenyl)-2-(3-fluorophenylsulfinyl)imidazole as an amorphous foam.

$C_{23}H_{19}FN_2O_3S$ (422.49): Calculated: 65.39% C, 4.53% H, 4.50% F, 6.63% N, 7.59% S. Found: 65.31% C, 4.62% H, 4.50% F, 6.54% N, 7.48% S.

EXAMPLE 42

A solution of 4.33 g of 3-chloroperbenzoic acid (80%) in 300 ml of dichloromethane is dropped to a solution of 4.07 g of 4,5-bis(4-methoxyphenyl)-2-(3-fluorophenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, yielding 3.99 g of 4,5-bis(4-methoxyphenyl)-2-(3-fluorophenylsulfonyl)imidazole as an amorphous foam.

$C_{23}H_{19}FN_2O_4S$ (438.49): Calculated: 63.00% C, 4.37% H, 4.33% F, 6.39% N, 7.31% S. Found: 62.88% C, 4.45% H, 4.26% F, 6.14% N, 7.19% S.

EXAMPLE 43

A solution of 2.164 g of 3-chloroperbenzoic acid (80%) in 150 ml of dichloromethane is added dropwise to a solution of 4.07 g of 4,5-bis(4-methoxyphenyl)-2-(2-fluorophenylthio)imidazole in 100 ml of dichloromethane. The solution is stirred for 3 hours at room temperature, washed with sodium bicarbonate solution, dried over sodium sulfate, and concentrated under vacuum to dryness. The residue is chromatographed on 150 g of silica gel with acetone/hexane, thus obtaining 3.49 g of 4,5-bis(4-methoxyphenyl)-2-(2-fluorophenylsulfinyl)imidazole as an amorphous foam.

$C_{23}H_{19}FN_2O_3S$ (422.49): Calculated: 65.39% C, 4.53% H, 4.50% F, 6.63% N, 7.59% S. Found: 65.28% C, 4.61% H, 4.55% F, 6.56% N, 7.43% S.

EXAMPLE 44

A solution of 4.33 g of 3-chloroperbenzoic acid (80%) in 300 ml of dichloromethane is dropped to a solution of 4.07 g of 4,5-bis(4-methoxyphenyl)-2-(2-fluorophenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, yielding 3.94 g of 4,5-bis(4-methoxyphenyl)-2-(2-fluorophenylsulfonyl)imidazole as an amorphous foam.

$C_{23}H_{19}FN_2O_4S$ (438.49): Calculated: 63.00% C, 4.37% H, 4.33% F, 6.39% N, 7.31% S. Found: 62.90% C, 4.45% H, 4.27% F, 6.43% N, 7.32% S.

EXAMPLE 45

A solution of 2.164 g of 3-chloroperbenzoic acid (80%) in 150 ml of dichloromethane is added dropwise to a solution of 4.19 g of 4,5-bis(4-methoxyphenyl)-2-(2-methoxyphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus producing 3.86 g of 4,5-bis(4-methoxyphenyl)-2-(2-methoxyphenylsulfinyl)imidazole as an amorphous foam.

$C_{24}H_{22}N_2O_4S$ (434.53): Calculated: 66.34% C, 5.10% H, 6.45% N, 7.38% S. Found: 66.23% C, 5.16% H, 6.39% N, 7.30% S.

EXAMPLE 46

A solution of 4.33 g of 3-chloroperbenzoic acid (80%) in 300 ml of dichloromethane is added dropwise to a solution of 4.19 g of 4,5-bis(4-methoxyphenyl)-2-(2-methoxyphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.72 g of 4,5-bis(4-methoxyphenyl)-2-(2-methoxyphenylsulfonyl)imidazole as an amorphous foam.

$C_{24}H_{22}N_2O_5S$ (450.53): Calculated: 63.99% C, 4.92% H, 6.22% N, 7.12% S. Found: 64.07% C, 5.04% H, 6.17% N, 7.02% S.

EXAMPLE 47

A solution of 2.164 g of 3-chloroperbenzoic acid (80%) in 150 ml of dichloromethane is dropped to a solution of 4.19 g of 4,5-bis(4-methoxyphenyl)-2-(4-methoxyphenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, yielding 3.92 g of 4,5-bis(4-methoxyphenyl)-2-(4-methoxyphenylsulfinyl)imidazole as an amorphous foam.

$C_{24}H_{22}N_2O_4S$ (434.53): Calculated: 66.34% C, 5.10% H, 6.45% N, 7.38% S. Found: 66.27% C, 5.17% H, 6.40% N, 7.42% S.

EXAMPLE 48

A solution of 4.33 g of 3-chloroperbenzoic acid (80%) in 300 ml of dichloromethane is added dropwise to a solution of 4.19 g of 4,5-bis(4-methoxyphenyl)-2-(4-methoxyphenylthio)imidazole in 100 ml of dichloromethane. The mixture is agitated for 3 hours at room temperature, the solution is washed with sodium bicarbonate solution, dried over sodium sulfate, and concentrated under vacuum to dryness. The residue is chromatographed on 150 g of silica gel with acetone/hexane, yielding 4.05 g of 4,5-bis(4-methoxyphenyl)-2-(4-methoxyphenylsulfonyl)imidazole as an amorphous foam.

$C_{24}H_{22}N_2O_5S$ (450.53): Calculated: 63.99% C, 4.92% H, 6.22% N, 7.12% S. Found: 63.86% C, 4.99% H, 6.25% N, 7.06% S.

EXAMPLE 49

A solution of 2.164 g of 3-chloroperbenzoic acid (80%) in 150 ml of dichloromethane is added dropwise to a solution of 4.19 g of 4,5-bis(4-methoxyphenyl)-2-(3-methoxyphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.96 g of 4,5-bis(4-methoxyphenyl)-2-(3-methoxyphenylsulfinyl)imidazole as an amorphous foam.

$C_{24}H_{22}N_2O_4S$ (434.53): Calculated: 66.34% C, 5.10% H, 6.45% N, 7.38% S. Found: 66.24% C, 5.15% H, 6.38% N, 7.33% S,

EXAMPLE 50

A solution of 4.33 g of 3-chloroperbenzoic acid (80%) in 300 ml of dichloromethane is dropped to a solution of 4.19 g of 4,5-bis(4-methoxyphenyl)-2-(3-methoxyphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus obtaining 4.02 g of 4,5-bis(4-methoxyphenyl)-2-(3-methoxyphenylsulfonyl)imidazole as an amorphous foam.

$C_{24}H_{22}N_2O_5S$ (450.53): Calculated: 63.99% C, 4.92% H, 6.22% N, 7.12% S. Found: 63.87% C, 5.03% H, 6.17% N, 7.09% S.

EXAMPLE 51

A solution of 2.164 g of 3-chloroperbenzoic acid (80%) in 150 ml of dichloromethane is added dropwise to a solution of 4.25 g of 4,5-bis(4-methoxyphenyl)-2-(2,4-difluorophenylthio)imidazole in 100 ml of dichloromethane. The mixture is agitated for 3 hours at room temperature, the solution washed with sodium bicarbonate solution, dried over sodium sulfate, and concentrated under vacuum to dryness. The residue is chromatographed on 150 g of silica gel with acetone/hexane, thus producing 3.26 g of 4,5-bis(4-methoxyphenyl)-2-(2,4-difluorophenylsulfinyl)imidazole as an amorphous foam.

$C_{23}H_{19}F_2N_2O_3S$ (440.47): Calculated: 62.72% C, 4.12% H, 8.63% F, 6.36% N, 7.28% S. Found: 62.59% C, 4.23% H, 8.55% F, 6.28% N, 7.21% S.

EXAMPLE 52

A solution of 4.33 g of 3-chloroperbenzoic acid (80%) in 300 ml of dichloromethane is dropped to a solution of 4.25 g of 4,5-bis(4-methoxyphenyl)-2-(2,4-difluorophenylthio)imidazole in 100 ml of dichloromethane. The solution is agiated for 3 hours at room temperature, washed with sodium bicarbonate solution, dried over sodium sulfate, and concentrated to dryness under vacuum. The residue is chromatographed on 150 g of silica gel with acetone/hexane, yielding 3.41 g of 4,5-bis(4-methoxyphenyl)-2-(2,4-difluorophenylsulfonyl)imidazole as an amorphous foam.

$C_{23}H_{18}F_2N_2O_4S$ (456.47): Calculated: 60.52% C, 3.97% H, 8.32% F, 6.14% N, 7.02% S. Found: 60.41% C, 4.07% H, 8.22% F, 6.03% N, 6.90% S.

EXAMPLE 53

A solution of 2.164 g of 3-chloroperbenzoic acid (80%) in 150 ml of dichloromethane is added dropwise to a solution of 4.57 g of 4,5-bis(4-methoxyphenyl)-2-(4-trifluoromethylphenylthio)imidazole in 100 ml of dichloromethane. The mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, thus producing 4.26 g of 4,5-bis(4-methoxyphenyl)-2-(4-trifluoromethylphenylsulfinyl)imidazole as an amorphous foam.

$C_{24}H_{19}F_3N_2O_3S$ (472.49): Calculated: 61.01% C, 4.05% H, 12.06% F, 5.93% N, 6.79% S. Found: 60.90% C, 4.13% H, 11.97% F, 6.02% N, 6.71% S.

EXAMPLE 54

A solution of 4.33 g of 3-chloroperbenzoic acid (80%) in 300 ml of dichloromethane is added dropwise to a solution of 4.57 g of 4,5-bis(4-methoxyphenyl)-2-(4-trifluoromethylphenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, thus obtaining 4.33 g of 4,5-bis(4-methoxyphenyl)-2-(4-trifluoromethylphenylsulfonyl)imidazole as an amorphous foam.

$C_{24}H_{19}F_3N_2O_4S$ (488.49): Calculated: 59.01% C, 3.92% H, 11.67% F, 5.73% N, 6.56% S. Found: 58.89% C, 4.00% H, 11.61% F, 5.68% N, 6.59% S.

EXAMPLE 55

A solution of 2.164 g of 3-chloroperbenzoic acid (80%) in 150 ml of dichloromethane is added dropwise to a solution of 4.67 g of 4,5-bis(4-methoxyphenyl)-2-(4-bromophenylthio)imidazole in 100 ml of dichloromethane. The reaction mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, yielding 4.36 g of 4,5-bis(4-methoxyphenyl)-2-(4-bromophenylsulfinyl)imidazole as an amorphous foam.

$C_{23}H_{19}BrN_2O_3S$ (483.39): Calculated: 57.15% C, 3.96% H, 16.53% Br, 5.80% N, 6.63% S. Found: 57.07% C, 4.07% H, 16.41% Br, 5.72% N, 6.58% S.

EXAMPLE 56

A solution of 4.33 g of 3-chloroperbenzoic acid (80%) in 300 ml of dichloromethane is added dropwise to a solution of 4.67 g of 4,5-bis(4-methoxyphenyl)-2-(4-bromophenylthio)imidazole in 100 ml of dichloromethane. The solution is agitated for 3 hours at room temperature, washed with sodium bicarbonate solution, dried over sodium sulfate, and concentrate to dryness under vacuum. The residue is chromatographed on 150 g of silica gel with acetone/hexane, thus obtaining 4.41 g of 4,5-bis(4-methoxyphenyl)-2-(4-bromophenylsulfonyl)imidazole as an amorphous foam.

$C_{23}H_{19}BrN_2O_4S$ (499.39): Calculated: 55.32% C, 3.83% H, 16.00% Br, 5.61% N, 6.42% S. Found: 55.27% C, 3.90% H, 15.79% Br, 5.54% N, 6.36% S.

EXAMPLE 57

A solution of 2.164 g of 3-chloroperbenzoic acid (80%) in 150 ml of dichloromethane is added dropwise to a solution of 4.23 g of 4,5-bis(4-methoxyphenyl)-2-(4-chlorophenylthio)imidazole in 100 ml of dichloromethane. The reaction mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, thus obtaining 3.90 g of 4,5-bis(4-methoxyphenyl)-2-(4-chlorophenylsulfinyl)imidazole as an amorphous foam.

$C_{23}H_{19}ClN_2O_3S$ (438.94): Calculated: 62.94% C, 4.36% H, 8.08% Cl, 6.38% N, 7.30% S. Found: 62.87% C, 4.42% H, 8.00% Cl, 6.26% N, 7.23% S.

EXAMPLE 58

A solution of 4.33 g of 3-chloroperbenzoic acid (80%) in 300 ml of dichloromethane is added dropwise to a solution of 4.23 g of 4,5-bis(4-methoxyphenyl)-2-(4-chlorophenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, yielding 3.93 g of 4,5-bis(4-methoxyphenyl)-2-(4-chlorophenylsulfonyl)imidazole as an amorphous foam.

$C_{23}H_{19}ClN_2O_4S$ (454.93): Calculated: 60.72% C, 4.21% H, 7.79% Cl, 6.16% N, 7.05% S. Found: 60.61% C, 4.28% H, 7.68% Cl, 6.09% N, 6.96% S.

EXAMPLE 59

A solution of 2.164 g of 3-chloroperbenzoic acid (80%) in 150 ml of dichloromethane is dropped to a solution of 4.03 g of 4,5-bis(4-methoxyphenyl)-2-(4-methylphenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.71 g of 4,5-bis(4-methoxyphenyl)-2-(4-methylphenylsulfinyl)imidazole as an amorphous foam.

$C_{24}H_{22}N_2O_3S$ (418.52): Calculated: 68.88% C, 5.30% H, 6.69% N, 7.66% S. Found: 68.75% C, 5.37% H, 6.60% N, 7.61% S.

EXAMPLE 60

A solution of 4.33 g of 3-chloroperbenzoic acid (80%) in 300 ml of dichloromethane is added dropwise to a solution of 4.03 g of 4,5-bis(4-methoxyphenyl)-2-(4-methylphenylthio)imidazole in 100 ml of dichloromethane, then agitated for 3 hours at room temperature, washed with sodium bicarbonate solution, dried over sodium sulfate, and concentrated to dryness under vacuum. The residue is chromatographed on 150 g of silica gel with acetone/hexane, thus producing 3.96 g of 4,5-bis(4-methoxyphenyl)-2-(4-methylphenylsulfonyl)imidazole as an amorphous foam.

$C_{24}H_{22}N_2O_4S$ (434.52): Calculated: 66.34% C, 5.10% H, 6.45% N, 7.38% S. Found: 66.29% C, 5.18% H, 6.45% N, 7.28% S.

EXAMPLE 61

A solution of 2.164 g of 3-chloroperbenzoic acid (80%) in 150 ml of dichloromethane is added dropwise to a solution of 4.45 g of 4,5-bis(4-methoxyphenyl)-2-(4-tert-butylphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus producing 4.17 g of 4,5-bis(4-methoxyphenyl)-2-(4-tert-butylphenylsulfinyl)imidazole as an amorphous foam.

$C_{27}H_{28}N_2O_3S$ (460.60): Calculated: 70.41% C, 6.13% H, 6.08% N, 6.96% S. Found: 70.36% C, 6.17% H, 6.01% N, 6.66% S.

EXAMPLE 62

A solution of 4.33 g of 3-chloroperbenzoic acid (80%) in 300 ml of dichloromethane is dropped to a solution of 4.45 g of 4,5-bis(4-methoxyphenyl)-2-(4-tert-butylphenylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, yielding 4.28 g of 4,5-bis(4-methoxyphenyl)-2-(4-tert-butylphenylsulfonyl)imidazole as an amorphous foam.

$C_{27}H_{22}N_2O_4S$ (476.60): Calculated: 68.04% C, 5.92% H, 5.88% N, 6.73% S. Found 67.92% C, 6.03% H, 5.69% N, 6.66% S.

EXAMPLE 63

A solution of 2.164 g of 3-chloroperbenzoic acid (80%) in 150 ml of dichloromethane is dropped to a solution of 4.46 g of 4,5-bis(4-methoxyphenyl)-2-(2-acetoamidophenylthio)imidazole in 100 ml of dichloromethane. The mixture is stirred for 3 hours at room temperature, the solution washed with sodium bicarbonate solution, dried over sodium sulfate, and concentrated to dryness under vacuum. The residue is chromatographed on 150 g of silica gel with acetone/hexane, thus obtaining 3.96 g of 4,5-bis(4-methoxyphenyl)-2-(2-acetamidophenylsulfinyl)imidazole as an amorphous foam.

$C_{25}H_{23}N_3O_3S$ (461.54): Calculated: 65.06% C, 5.02% H, 9.10% N, 6.95% S. Found: 64.95% C, 5.13% H, 9.01% N, 6.88% S.

EXAMPLE 64

A solution of 4.33 g of 3-chloroperbenzoic acid (80%) in 300 ml of dichloromethane is added dropwise to a solution of 4.46 g of 4,5-bis(4-methoxyphenyl)-2-(2-acetamidophenylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, thus producing 4.21 g of 4,5-bis(4-methoxyphenyl)-2-(2-acetamidophenylsulfonyl)imidazole as an amorphous foam.

$C_{25}H_{23}N_3O_5S$ (477.54): Calculated: 62.88% C, 4.85% H, 8.80% N, 6.71% S. Found: 62.80% C, 4.96% H, 8.77% N, 6.66% S.

EXAMPLE 65

A solution of 2.164 g of 3-chloroperbenzoic acid (80%) in 150 ml of dichloromethane is added dropwise to a solution of 4.03 g of 4,5-bis(4-methoxyphenyl)-2-phenylthio-1-methylimidazole in 100 ml of dichloromethane. The solution is agitated for 3 hours at room temperature, washed with sodium bicarbonate solution, dried over sodium sulfate, and concentrated to dryness under vacuum. The residue is chromatographed on 200 g of silica gel with ethyl acetate/cyclohexane 2:3, thus obtaining 3.05 g of 4,5-bis(4-methoxyphenyl)-2-phenylsulfinyl-1-methylimidazole, which has a melting point of 114°–115° after recrystallization from dichloromethane/ether.

EXAMPLE 66

A solution of 4.33 g of 3-chloroperbenzoic acid (80%) in 300 ml of dichloromethane is added dropwise to a solution of 4.03 g of 4,5-bis(4-methoxyphenyl)-2-phenylthio-1-methylimidazole in 100 ml of dichloromethane. The reaction mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, thus obtaining after recrystallization from dichloromethane/cyclohexane 3.19 g of 4,5-bis(4-methoxyphenyl)-2-(2-thiazolylsulfonyl)imidazole, mp 148°–150°.

EXAMPLE 67

A solution of 2.164 g of 3-chloroperbenzoic acid (80%) in 150 ml of dichloromethane is added dropwise to a solution of 3.90 g of 4,5-bis(4-methoxyphenyl)-2-(2-pyridylthio)imidazole in 100 ml of dichloromethane. The solution is stirred for 3 hours at room temperature, washed with sodium bicarbonate solution, dried over sodium sulfate, and concentrated under vacuum to dryness. The residue is chromatographed on 150 g of silica gel with acetone/hexane, thus producing 3.42 g of 4,5-bis(4-methoxyphenyl)-2-(2-pyridylsulfinyl)imidazole as an amorphous foam.

$C_{22}H_{19}N_3O_3S$ (405.48): Calculated: 65.17% C, 4.72% H, 10.36% N, 7.91% S. Found: 65.07% C, 4.83% H, 10.21% N, 7.79% S.

EXAMPLE 68

A solution of 4.33 g of 3-chloroperbenzoic acid (80%) in 300 ml of dichloromethane is added dropwise to a solution of 3.90 g of 4,5-bis(4-methoxyphenyl)-2-(2-pyridylthio)imidazole in 100 ml of dichloromethane. The reaction mixture is stirred for 3 hours at room temperature, the solution washed with sodium bicarbonate solution, dried over sodium sulfate, and concentrated to dryness under vacuum. The residue is chromatographed on 150 g of silica gel with acetone/hexane, thus producing 3.44 g of 4,5-bis(4-methoxyphenyl)-2-(2-pyridylsulfonyl)imidazole as an amorphous foam.

$C_{22}H_{19}N_3O_4S$ (421.48): Calculated: 62.69% C, 4.54% H, 9.97% N, 7.61% S. Found: 62.66% C, 4.66% H, 9.89% N, 7.54% S.

EXAMPLE 69

A solution of 2.164 g of 3-chloroperbenzoic acid (80%) in 150 ml of dichloromethane is added dropwise to a solution of 3.91 g of 4,5-bis(4-methoxyphenyl)-2-(2-pyrimidinylthio)imidazole in 100 ml of dichloromethane. The mixture is stirred for 3 hours at room temperature, the solution is washed with sodium bicarbonate solution, dried over sodium sulfate, and concentrated to dryness under vacuum. The residue is chromatographed on 150 g of silica gel with acetone/hexane, thus producing 3.52 g of 4,5-bis(4-methoxyphenyl)-2-(2-pyrimidinylsulfinyl)imidazole as an amorphous foam.

$C_{21}H_{18}N_4O_3S$ (406.47): Calculated: 62.06% C, 4.46% H, 13.78% N, 7.89% S. Found: 62.15% C, 4.40% H, 13.70% N, 7.79% S.

EXAMPLE 70

A solution of 4.33 g of 3-chloroperbenzoic acid (80%) in 300 ml of dichloromethane is added dropwise to a solution of 3.91 g of 4,5-bis(4-methoxyphenyl)-2-(2-pyrimidinylthio)imidazole in 100 ml of dichloromethane. The solution is agitated for 3 hours at room temperature, washed with sodium bicarbonate solution, dried over sodium sulfate, and concentrated to dryness under vacuum. The residue is chromatographed on 150 g of silica gel with acetone/hexane, thus obtaining 3.54 g of 4,5-bis(4-methoxyphenyl)-2-(2-pyrimidinylsulfonyl)imidazole as an amorphous foam.

$C_{21}H_{18}N_4O_4S$ (422.47): Calculated: 59.71% C, 4.29% H, 13.26% N, 7.59% S. Found: 59.62% C, 4.40% H, 13.15% N, 7.49% S.

EXAMPLE 71

6.43 g of 4,5-bis(4-chlorophenyl)-2-mercaptoimidazole is dissolved in 150 ml of absolute dimethylformamide and combined with 0.6 g of sodium hydride (80% strength in white oil). The mixture is agitated for another 30 minutes, and then 4.25 g of 2-iodothiophene in 30 ml of dimethylformamide is added dropwise thereto; the mixture is heated under reflux for 16 hours under argon. The solution is then poured into 600 ml of ice water, the product is extracted with ethyl acetate; the organic solution is dried over sodium sulfate and concentrated to dryness under vacuum. The residue is recrystallized from ether, yielding 7.02 g of 4,5-bis(4-chlorophenyl)-2-(2-thienylthio)imidazole, mp 219°.

EXAMPLE 72

A solution of 2.164 g of 3-chloroperbenzoic acid (80%) in 150 ml of dichloromethane is added dropwise to a solution of 4.90 g of 4,5-bis(4-chlorophenyl)-2-(2-thienylthio)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, yielding 3.83 g of 4,5-bis(4-chlorophenyl)-2-(2-thienylsulfinyl)imidazole as an amorphous foam.

$C_{19}H_{22}Cl_2N_2OS$ (455.47): Calculated: 50.11% C, 2.66% H, 15.57% Cl, 6.15% N, 14.08% S. Found: 49.98% C, 2.77% H, 15.44% Cl, 6.08% N, 13.97% S.

EXAMPLE 73

A solution of 4.33 g of 3-chloroperbenzoic acid (80%) in 300 ml of dichloromethane is added dropwise to a solution of 4.40 g of 4,5-bis(4-chlorophenyl)-2-(2-thienylthio)imidazole in 100 ml of dichloromethane. The mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, thus obtaining 3.83 g of 4,5-bis(4-chlorophenyl)-2-(2-thienyl-sulfonyl)imidazole as an amorphous foam.

$C_{19}H_{12}Cl_2N_2O_2S_2$(471.47): Calculated: 48.40% C, 2.57% H, 15.04% Cl, 5.94% N, 13.60% S. Found 48.21% C, 2.68% H, 15.12% Cl, 5.82% N, 13.51% S.

EXAMPLE 74

3.12 g of 4,5-bis(4-methoxyphenyl)-2-mercap-toimidazole is dissolved in 100 ml of absolute dimethyl-formamide and combined with 0.6 g of sodium hydride (80% strength in white oil). The mixture is further agitated for 30 minutes, and then 1.52 g of 4-chloropyridine hydrochloride is added. The mixture is refluxed under argon for 16 hours. Then the solution is poured into 300 ml of ice water, the product is extracted with ethyl acetate, the organic solution is dried over sodium sulfate and concentrated to dryness under vacuum. The residue is recrystallized from acetone/ether, thus obtaining 3.19 g of 4,5-bis(4-methoxyphenyl)-2-(4-pyridylthi-o)imidazole, mp 177°–179°.

EXAMPLE 75

A solution of 2.164 g of 3-chloroperbenzoic acid (80%) in 150 ml of dichloromethane is added dropwise to a solution of 3.90 g of 4,5-bis(4-methoxyphenyl)-2-(4-pyridylthio)imidazole in 100 ml of dichloromethane. The mixture is agitated for 3 hours at room temperature, the solution is washed with sodium bicarbonate solution, dried over sodium sulfate, and concentrated to dryness under vacuum. The residue is recrystallized from ethanol/ether, thus producing 3.41 g of 4,5-bis(4-methoxyphenyl)-2-(4-pyridylsulfinyl)imidazole, mp 170°–171°.

$C_{24}H_{22}N_2O_3S$ (418.52): Calculated: 68.88% C, 5.30% H, 6.69% N, 7.66% S. Found: 68.75% C, 5.37% H, 6.60% N, 7.61% S.

EXAMPLE 76

A solution of 4.33 g of 3-chloroperbenzoic acid (80%) in 300 ml of dichloromethane is dropped to a solution of 3.90 g of 4,5-bis(4-methoxyphenyl)-2-(4-pyridylthi-o)imidazole in 100 ml of dichloromethane. The solution is stirred for 3 hours at room temperature, washed with sodium bicarbonate solution, dried over sodium sulfate, and concentrated to dryness under vacuum. The residue is chromatographed on 150 g of silica gel with acetone/hexane, thus yielding 3.48 g of 4,5-bis(4-methoxy-phenyl)-2-(4-pyridylsulfonyl)imidazole as an amorphous foam.

$C_{22}H_{19}N_3O_5S$ (421.48): Calculated: 62.69% C, 4.54% H, 9.97% N, 7.61% S. Found: 62.58% C, 4.49% H, 9.90% N, 7.53% S.

EXAMPLE 77

3.12 g of 4,5-bis(4-methoxyphenyl)-2-mercap-toimidazole is added to a solution of 230 mg of sodium in 100 ml of absolute ethanol and, after dissolution, 3.61 g of diphenyl iodonium bromide is added to the mixture. The latter is heated under reflux for 2 hours, then combined with 115 mg of sodium as well as another 1.81 g of diphenyl iodonium bromide, and the mixture is once again heated under reflux for 2 hours. The mixture is then allowed to cool, poured into 300 ml of ice water, the product is taken up in ethyl acetate, the organic solution is dried over sodium sulfate and concentrated under vacuum. The iodobenzene is removed by codistillation with toluene. The residue is crystallized from hexane/ethyl acetate, thus obtaining 3.34 g of 4,5-bis(4-methoxyphenyl)-2-(phenylthio)imidazole, mp 177°–179°.

EXAMPLE 78

Under agitation and with argon as the protective gas, 7 ml of about 1.5N n-butyllithium in hexane, diluted with 10 ml of benzene, is added dropwise at −5° to 0° to a solution of 3.65 g of 4,5-bis(4-methoxyphenyl)-1-(tetrahydropyran-2-yl)imidazole in a mixture of 50 ml of absolute ether and 50 ml of benzene. After 20 minutes, a solution of 2.65 g of p-tolylsulfinic acid p-toluthiol ester in 30 ml of absolute ether is added dropwise thereto, while maintaining the temperature at between −5° and 0° by cooling. After 6 hours of agitation at room temperature, the mixture is poured into 800 ml of water. The product is taken up in ethyl acetate, the organic solution is dried over sodium sulfate and concentrated to dryness. The residue is chromatographed on 250 g of aluminum oxide, neutral, activity stage II, with ethyl acetate/hexane 2:3, thus producing a nonpolar fraction yielding after crystallization from ether 1.58 g of 4,5-bis(4-methoxyphenyl)-1-(tetrahydropyran-2-yl)-2-(4-methylphenylthio)imidazole, mp 192°, and a more polar fraction yielding after crystallization from ether/hexane 1.09 g of 4,5-bis(4-methoxyphenyl)-1-(tetrahydropyran-2-yl)-2-(4-methylphenylsulfinyl-)imidazole, mp 149°–151°.

The blocking groups are split off as described in Example 22, thus obtaining from the thio compound 1.23 g of 4,5-bis(4-methoxyphenyl)-2-(4-methylphenylthi-o)imidazole, mp 181° after recrystallization from ether; and from the sulfinyl compound 0.83 g of 4,5-bis(4-methoxyphenyl)-2-(4-methylphenylsulfinyl)imidazole, mp 162°–164° after recrystallization from ethanol/ether.

Production of the p-tolylsulfinic acid p-toluthiol ester:

Under agitation, a solution of 4.74 g (about 75%) 3-chloroperbenzoic acid in 500 ml of dichloromethane is added dropwise at 0° to a solution of 4.93 g of 4,4'-dimethyldiphenyldisulfide in 50 ml of dichloromethane. A precipitate is thus produced which is dissolved by adding 30 ml of absolute tetrahydrofuran. After 5 hours, the mixture is washed with ice-cold sodium bicarbonate solution, dried over sodium sulfate, and concentrated to dryness under vacuum. The residue is taken up in ether and crystallized at +4°. Yield: 3.12 g of p-tolylsulfinic acid p-toluthiol ester, mp 91°.

EXAMPLE 79

Under agitation and using argon as the protective gas, 7 ml approximately 1.5N n-butyllithium in hexane is added dropwise at 0° to a solution of 3.71 g of 4,5-bis(4-methoxyphenyl)-1-benzylimidazole in a mixture of 50 ml of absolute ether and 50 ml of benzene. After 30 minutes, a suspension of 3.3 g of p-toluenesulfonic acid anhydride in 50 ml of absolute ether/benzene 1:1 is added dropwise to the reaction mixture, maintaining the temperature between −5° and 0° by cooling. After 16 hours of agitation at room temperature, the reaction mixture is washed with sodium bicarbonate solution; the organic solution is dried over sodium sulfate and concentrated to dryness under vacuum. The residue is recrystallized from ether, yielding 3.78 g of 4,5-bis(4-methoxyphenyl)-1-benzyl-2-(4-methylphenylsulfonyl-)imidazole, mp 154°–156°.

EXAMPLE 80

Under agitation and with argon as the protective gas, 17.5 ml of 15% strength n-butyllithium in hexane, diluted with 30 ml of ether, is added dropwise at −5° to 0° to a suspension of 9.26 g of 4,5-bis(4-methoxyphenyl)-1-benzylimidazole in a mixture of 30 ml of absolute ether and 30 ml of benzene. After 10 minutes, a solution of 6.16 g of 4,4'-dimethyldiphenyldisulfide in 50 ml of absolute ether is added dropwise to the reaction mixture under cooling to keep the temperature between −5° and 0°. After 3 hours of agitation at room temperature, the mixture is diluted with ethyl acetate, the thiol is extracted with sodium hydroxide solution, the organic phase is washed with water; the organic solution is dried over sodium sulfate and concentrated to dryness under vacuum. The residue is recrystallized from ether, thus obtaining 9.94 g of 4,5-bis(4-methoxyphenyl)-1-benzyl-2-(4-methylphenylthio)imidazole, mp 115°–117°.

EXAMPLE 81

A solution of 1.08 g of 3-chloroperbenzoic acid (80%) in 100 ml of dichloromethane is added dropwise to a solution of 2.46 g of 4,5-bis(4-methoxyphenyl)-1-benzyl-2-(4-methylphenylthio)imidazole in 50 ml of dichloromethane. The mixture is stirred for 3 hours at room temperature, the solution is washed with sodium bicarbonate solution, dried over sodium sulfate, and concentrated to dryness under vacuum. The residue is chromatographed on 150 g of silica gel with ethyl acetate/hexane 2:3, thus producing 2.17 g of 4,5-bis-(4-methoxyphenyl)-1-benzyl-2-(4-methylphenylsulfinyl)imidazole as an amorphous foam.

$C_{31}H_{28}N_2O_3S$ (508.64): Calculated: 73.20% C, 5.55% H, 5.51% N, 6.30% S. Found: 73.00% C, 5.72% H, 5.43% N, 6.21% S.

EXAMPLE 82

2.164 g of 3-chloroperbenzoic acid (80%) is added in incremental portions to a solution of 2.46 g of 4,5-bis-(4-methoxyphenyl)-1-benzyl-2-(4-methylphenylthio)imidazole in 250 ml of dichloromethane. The mixture is stirred for 1 hour at room temperature, the solution is washed with sodium bicarbonate solution, dried over sodium sulfate, and concentrated to dryness under vacuum. The residue is recrystallized from ether, thus obtaining 3.96 g of 4,5-bis(4-methoxyphenyl)-1-benzyl-2-(4-methylphenylsulfonyl)imidazole, mp 154°–156°.

EXAMPLE 83

Three drops of triethylamine is added to a solution of 4.85 g of pentafluorothiophenol in 35 ml of carbon tetrachloride. Then, 2.07 ml of sulfuryl chloride in 35 ml of carbon tetrachloride is added dropwise at 0°. The mixture is stirred for another 30 minutes at 0°, then the solvent is removed under vacuum, and residual solvent is withdrawn by codistillation with absolute toluene. The mixture is taken up in 30 ml of toluene, decanted off from triethylammonium hydrochloride, and the thus-obtained pentafluorophenylsulfenyl chloride is used in the subsequent reaction stage without further purification.

Under agitation and using argon as the protective gas, 15 ml of about 1.6N n-butyllithium in hexane, diluted with 30 ml of toluene, is added dropwise at −5° to 0° to a solution of 8.83 g of 4,5-bis(4-methoxyphenyl)-1-(tetrahydropyran-2-yl)imidazole in a mixture of 75 ml of absolute tetrahydrofuran and 75 ml of toluene. After 20 minutes, the pentafluorophenylsulfenyl chloride solution is added dropwise to the reaction mixture, maintaining the temperature between −5° and 0° by cooling. After 2 hours' stirring at room temperature, the solution is diluted with 200 ml of ethyl acetate, washed with sodium bicarbonate solution; the organic solution is dried over sodium sulfate and concentrated to dryness under vacuum. The residue is purified by chromatography on aluminum oxide, neutral, activity stage II, with hexane/ethyl acetate. Recrystallization from ethyl acetate/hexane yields 8.86 g of 4,5-bis(4-methoxyphenyl)-1-(tetrahydropyran-2-yl)-2-(pentafluorophenylthio)imidazole, mp 156°–158°.

A solution is prepared from 5.63 g of the compound in 100 ml of ethanol; the mixture is combined with 5 ml of concentrated hydrochloric acid in 50 ml of ethanol and briefly heated on a water bath, whereupon a crystalline slurry begins to separate. The mixture is allowed to cool down, the crystals are vacuum-filtered and washed with alcohol, thus producing 5.35 g of 4,5-bis(4-methoxyphenyl)-2-(pentafluorophenylthio)imidazole hydrochloride, decomposition point 246°–248°.

EXAMPLE 84

Under argon and with agitation, 7 ml of 1.5N n-butyllithium in hexane, diluted with 10 ml of toluene, is added dropwise at 0° to a solution of 3.51 g of 4,5-bis(4-methoxyphenyl)-1-(tetrahydrofuran-2-yl)imidazole in a mixture of 80 ml of absolute ether and 40 ml of toluene. After 20 minutes, a solution of 2.19 g of diphenyldisulfide in 15 ml of absolute ether is added dropwise to the reaction mixture, during which step the temperature does not exceed 20°. After 2 hours of agitation at room temperature, the solution is extracted with 2N sodium hydroxide solution. The organic solution is concentrated to dryness under vacuum. The residue is chromatographed on 150 g of aluminum oxide, neutral, activity stage II. With ethyl acetate/hexane, 3.86 g of 4,5-bis(4-methoxyphenyl)-1-(tetrahydrofuran-2-yl)-2-phenylthioimidazole is eluted as an amorphous foam.

$C_{27}H_{26}N_2O_3S$ (458.58): Calculated: 70.72% C, 5.71% H, 6.11% N, 6.99% S. Found: 70.55% C, 5.80% H, 6.00% N, 6.88% S.

The compound is dissolved in 50 ml of glacial acetic acid/water and heated for 10 minutes on a water bath. The solvent is removed under vacuum, residual amounts of acetic acid are removed by codistillation with ethanol, and the residue is crystallized from ethyl acetate/hexane, thus obtaining 3.08 g of 4,5-bis(4-methoxyphenyl)-2-phenylthioimidazole, mp 177°–179°.

Production of 4,5-bis(4-methoxyphenyl)-1-(tetrahydrofuran-2-yl)imidazole:

5.61 g of 4,5-bis(4-methoxyphenyl)imidazole is suspended in 150 ml of absolute 1,2-dichloroethane and combined with 2.8 g of 2,3-dihydrofuran as well as 0.2 ml of tin tetrachloride. The mixture is heated under agitation for 12 hours to 70°, allowed to cool, and poured into 200 ml of cold sodium bicarbonate solution. The organic phase is separated, dried over sodium sulfate, and concentrated under vacuum. The residue is dissolved in dichloromethane and subjected to a hexane precipitation. The precipitate is subjected to column chromatography on 250 g of aluminum oxide, neutral, activity stage II. Elution with ethyl acetate/hexane 2:3 yields 5.39 g of 4,5-bis(4-methoxyphenyl)-1-(tetrahydrofuran-2-yl)imidazole, which is obtained in the form of a foam after removal of the solvent.

$C_{21}H_{22}N_2O_3$ (350.420): Calculated: 71.98% C, 6.33% H, 7.99% N. Found: 72.03% C, 6.40% H, 7.91% N.

EXAMPLE 85

6.25 g of 4,5-bis(4-methoxyphenyl)-2-mercaptoimidazole is dissolved in 150 ml of absolute dimethylformamide and combined with 0.60 g of sodium hydride (80% in oil). After the evolution of hydrogen has ceased, the solution is cooled to 0°, combined with a pinch of powdered copper, and then a diazonium salt solution, cooled to 0° and prepared from 3.26 g of 4-trifluoromethylaniline (99%), 1.38 g of sodium nitrite, as well as 10 ml of 6N hydrochloric acid, is added dropwise to the reaction mixture. The latter is agitated for 30 minutes at 0° and then allowed to warm up to room temperature. The solution is then concentrated under vacuum, the residue is distributed between water and ethyl acetate; the organic solution is dried over sodium sulfate and concentrated to dryness under vacuum. The residue is chromatographed on 500 g of aluminum oxide, neutral, activity stage II, with hexane/ethyl acetate 3:2 as the eluting agent. Elution yields 3.39 g of 4,5-bis(4-methoxyphenyl)-2-(4-trifluoromethylphenylthio)imidazole, mp 179°–181°.

EXAMPLE 86

Under the conditions of Example 85, 6.25 g of 4,5-bis(4-methoxyphenyl)-2-mercaptoimidazole is reacted in 150 ml of dimethylformamide in the presence of a pinch of powdered copper with 0.60 g of sodium hydride (80% in oil) and a diazonium salt solution prepared from 3.26 g of 3-trifluoromethylaniline (99%), 1.38 g of sodium nitrite, as well as 10 ml of 6N hydrochloric acid. Chromatography according to Example 85 yields 3.27 g of 4,5-bis(4-methoxyphenyl)-2-(3-trifluoromethylphenylthio)imidazole as an amorphous foam.

$C_{23}H_{19}F_3N_2O_2S$: Calculated: 62.15% C, 4.31% H, 12.82% F, 6.30% N, 7.21% S. Found: 62.21% C, 4.38% H, 12.76% F, 6.21% N, 7.14% S.

EXAMPLE 87

A solution of 2.164 g of 3-chloroperbenzoic acid (80%) in 150 ml of dichloromethane is added dropwise to a solution of 4.57 g of 4,5-bis(4-methoxyphenyl)-2-(4-trifluoromethylphenylthio)imidazole in 100 ml of dichloromethane. The mixture is agitated for 3 hours at room temperature, the solution is washed with sodium bicarbonate solution, dried over sodium sulfate, and concentrated to dryness under vacuum. The residue is chromatographed on 150 g of silica gel with acetone/hexane, thus producing 3.78 g of 4,5-bis-(4-methoxyphenyl)-2-(4-trifluoromethylphenylsulfinyl)imidazole as an amorphous foam.

$C_{24}H_{19}F_3N_2O_3S$ (472.49): Calculated: 61.01% C, 4.05% H, 12.06% F, 5.93% N, 6.79% S. Found: 60.82% C, 3.90% H, 11.98% F, 5.91% N, 6.80% S.

EXAMPLE 88

A solution of 4.33 g of 3-chloroperbenzoic acid in 300 ml of dichloromethane is added dropwise to a solution of 4.57 g of 4,5-bis(4-methoxyphenyl)-2-(3-trifluoromethylphenylthio)imidazole in 100 ml of dichloromethane. The solution is agitated for 3 hours at room temperature, washed with sodium bicarbonate solution, dried over sodium sulfate, and concentrated under vacuum to dryness. The residue is chromatographed on 150 g of silica gel with acetone/hexane, thus obtaining 4.33 g of 4,5-bis(4-methoxyphenyl)-2-(3-trifluoromethylphenylsulfonyl)imidazole as an amorphous foam.

$C_{24}H_{19}F_3N_2O_4S$ (488.49): Calculated: 59.01% C, 3.92% H, 11.67% F, 5.73% N, 6.56% S. Found: 59.12% C, 4.03% H, 11.68% F, 5.73% N, 6.54% S.

EXAMPLE 89

0.6 g of sodium hydride (80% in oil) is added to a solution of 3.12 g of 4,5-bis(4-methoxyphenyl)-2-mercaptoimidazole in 150 ml of absolute dimethylformamide. After the evolution of hydrogen has ceased, the mixture is further agitated for 20 minutes, and 1.76 g of 2-chloropyridine-N-oxide hydrochloride is added in incremental portions under agitation. The mixture is stirred for another hour at room temperature, the solvent is removed under vacuum, the mixture is diluted with a small amount of ethanol, poured into 200 ml of ice water, and the thus-precipitated product is taken up in dichloromethane. The organic solution is dried over sodium sulfate, concentrated to dryness under vacuum, and crystallized from dichloromethane/hexane, yielding 3.06 g of 4,5-bis(4-methoxyphenyl)-2-(N-oxy-2-pyridylthio)imidazole, mp 215°–217°.

EXAMPLE 90

7.5 g of 3-chloroperbenzoic acid (80%) in 600 ml of dichloromethane is added to a solution of 3.90 g of 4,5-bis(4-methoxyphenyl)-2-(2-pyridylthio)imidazole in 100 ml of dichloromethane. The mixture is stirred for 7 days at room temperature, the solution is washed with sodium bicarbonate solution, dried with sodium sulfate, and concentrated to dryness under vacuum. The residue is chromatographed on 150 g of silica gel with acetone/hexane 2:3 as the eluent. Yield: 2.88 g of 4,5-bis(4-methoxyphenyl)-2-(N-oxy-2-pyridylsulfonyl)imidazole, which has a decomposition point of 261°–263° after recrystallization from acetone.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating inflammation in a patient in need of such treatment comprising administering to the patient an antiinflammatorily effective amount of a compound of the formula

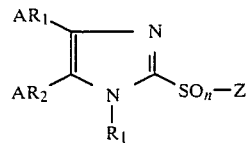

wherein
$AR_1$ and $AR_2$ each independently is phenyl;
$R_1$ is hydrogen or alkyl of 1–6 carbon atoms;
n is 0, 1 or 2; and
Z is phenyl substituted by nitro or nitro and halogen, $C_{1-4}$-alkyl, $C_{1-4}$-alkoxy, amino, $C_{1-6}$-alkanoylamino or trifluoromethyl;
or a physiologically acceptable salt thereof with an acid.

2. A method of claim 1 wherein $R_1$ is alkyl of 1–6 carbon atoms.

3. A method of claim 1, wherein Z is phenyl substituted by nitro and halogen, alkyl, alkoxy, amino, alkanoylamino or trifluoromethyl.

* * * * *